(12) United States Patent
Gordon

(10) Patent No.: US 11,123,176 B2
(45) Date of Patent: Sep. 21, 2021

(54) APPARATUS AND METHOD FOR REPAIR OF DISRUPTIONS BETWEEN BONES

(71) Applicant: Leonard Gordon, San Francisco, CA (US)

(72) Inventor: Leonard Gordon, San Francisco, CA (US)

(73) Assignee: PONTIS ORTHOPAEDICS LLC, San Francisco, CA (US)

( * ) Notice: Subject to any disclaimer, the term of this patent is extended or adjusted under 35 U.S.C. 154(b) by 0 days.

(21) Appl. No.: 15/530,862

(22) Filed: Mar. 10, 2017

(65) Prior Publication Data

US 2017/0258572 A1   Sep. 14, 2017

Related U.S. Application Data

(60) Provisional application No. 62/307,564, filed on Mar. 13, 2016.

(51) Int. Cl.
*A61F 2/42* (2006.01)
*A61B 17/17* (2006.01)
*A61F 2/08* (2006.01)

(52) U.S. Cl.
CPC ........ *A61F 2/0811* (2013.01); *A61B 17/1775* (2016.11); *A61B 17/1782* (2016.11); *A61F 2/4261* (2013.01); *A61F 2002/0823* (2013.01); *A61F 2002/0829* (2013.01); *A61F 2002/0835* (2013.01); *A61F 2002/0841* (2013.01); *A61F 2002/0864* (2013.01); *A61F 2002/0882* (2013.01); *A61F 2002/4292* (2013.01)

(58) Field of Classification Search
CPC ...... A61F 2002/0823; A61F 2002/0829; A61F 2002/0835; A61F 2002/0841; A61F 2002/0864; A61F 2002/0882; A61F 2/4261; A61F 2002/4292; A61B 2017/0448; A61B 2017/045; A61B 2017/0451; A61B 2017/0453; A61B 2017/0454; A61B 2017/0462; A61B 17/8866

See application file for complete search history.

(56) References Cited

U.S. PATENT DOCUMENTS

| 630,428 | A | | 8/1899 | Wahlert |
| 3,361,460 | A | | 1/1968 | Jansen |
| 4,828,562 | A | * | 5/1989 | Kenna ............ A61F 2/0811 |
| | | | | 623/13.13 |

(Continued)

FOREIGN PATENT DOCUMENTS

| DE | 102005005135 A1 * | 8/2006 | ............ A61F 2/0811 |
| DE | 102005054708 A1 * | 5/2007 | ............ A61F 2/0811 |
| WO | WO-2014141253 A1 * | 9/2014 | ......... A61B 17/8863 |

*Primary Examiner* — Javier G Blanco
(74) *Attorney, Agent, or Firm* — Law Office of Michael D. Yablonsky, LLC; Michael D. Yablonsky, Esq

(57) ABSTRACT

An apparatus and method for the repair of disruptions between bones. The apparatus defines a combination of sleeves, strands and crimps are provided to secure the bones, using a dual sided drill guide to prepare the bones for installation of the apparatus, which is adjusted upon installation to suit the appropriate alignment and tension of the apparatus. The method includes the preparation of the bones, the installation of the apparatus and the adjustment of the apparatus to properly align and tension the apparatus for repair of the bone.

4 Claims, 8 Drawing Sheets

(56) References Cited

U.S. PATENT DOCUMENTS

| | | | |
|---|---|---|---|
| 5,061,137 A * | 10/1991 | Gourd | F16B 19/00 411/392 |
| 5,569,253 A | 10/1996 | Farris | |
| 5,702,397 A * | 12/1997 | Goble | A61B 17/0401 606/232 |
| 6,053,921 A | 4/2000 | Wagner | |
| 6,272,273 B1 | 8/2001 | Bookwalter | |
| 6,573,452 B2 | 6/2003 | Karlsson | |
| 6,994,725 B1 * | 2/2006 | Goble | A61B 17/1714 606/232 |
| 7,172,595 B1 * | 2/2007 | Goble | A61B 17/1714 606/86 A |
| 7,491,217 B1 * | 2/2009 | Hendren | A61B 17/0401 606/232 |
| 7,955,388 B2 * | 6/2011 | Jensen | A61B 17/8685 623/13.14 |
| 8,114,129 B2 * | 2/2012 | Lubbers | A61B 17/0401 606/103 |
| 8,114,135 B2 | 2/2012 | Malandain | |
| 8,469,966 B2 | 6/2013 | Allen | |
| 8,608,742 B2 | 12/2013 | Dell'Oca | |
| 8,715,348 B2 * | 5/2014 | McNamara | A61B 17/0401 606/301 |
| 8,795,343 B2 | 8/2014 | Stucki | |
| 9,164,233 B2 | 10/2015 | Wouters | |
| 9,439,698 B2 | 9/2016 | Songer | |
| 2004/0024456 A1 * | 2/2004 | Brown, Jr. | A61B 17/0401 623/13.15 |
| 2004/0127907 A1 * | 7/2004 | Dakin | A61B 17/842 606/62 |
| 2004/0193217 A1 * | 9/2004 | Lubbers | A61B 17/0401 606/232 |
| 2004/0199169 A1 | 10/2004 | Koons | |
| 2005/0159812 A1 * | 7/2005 | Dinger, III | A61F 2/0811 623/13.14 |
| 2008/0082130 A1 * | 4/2008 | Ward | A61B 17/0401 606/232 |
| 2008/0288070 A1 * | 11/2008 | Lo | A61B 17/0401 623/13.14 |
| 2012/0065648 A1 * | 3/2012 | Roorda | A61B 17/0487 606/148 |
| 2014/0194907 A1 * | 7/2014 | Bonutti | A61B 17/683 606/151 |
| 2014/0222073 A1 * | 8/2014 | Taylor | A61B 17/0487 606/233 |
| 2016/0038186 A1 * | 2/2016 | Herzog | A61B 17/685 606/304 |
| 2016/0354196 A1 * | 12/2016 | Tepic | A61B 17/0401 |

\* cited by examiner

APPARATUS AND METHOD FOR REPAIR OF DISRUPTIONS BETWEEN BONES

CROSS REFERENCE TO RELATED APPLICATIONS

Applicant claims the benefit of U.S. Provisional Patent Application No. 62/307,564, filed on Mar. 13, 2016, by the same inventor.

I. BACKGROUND OF THE INVENTION

1. Field of Invention

An apparatus and method for the repair of disruptions between bones and connecting soft tissues. The apparatus defines a combination of sleeves, strands and crimps are provided to secure the bones, using a dual sided drill guide to prepare the bones for installation of the apparatus, which is adjusted upon installation to suit the appropriate alignment and tension of the apparatus. The method includes the preparation of the bones, the installation of the apparatus and the adjustment of the apparatus to properly align and tension the apparatus for repair of the bone or soft tissue.

2. Description of Prior Art

A preliminary review of prior art patents was conducted by the applicant which reveal prior art patents in a similar field or having similar use. Many surgical apparatus, methods and techniques are know to those skilled in the art of surgery, especially to those familiar with the involved surgical sites and bone repairs disclosed herein and as mentioned not only in this section but in those subsequently disclosed in those sections below. While each known apparatus may prove to suit the needs of the patient and the desire of the surgeon, they do not disclose the same or similar elements as the present bone disruption repair apparatus, nor do they present the material components in a manner contemplated or anticipated in the prior art.

In two U.S. Pat. No. 3,361,460 to Jansen and U.S. Pat. No. 630,428 to Wahlert, compression fittings are shown as applied to pipes or wires which demonstrate a tapered threaded sectional fitting which compresses an inner diameter when inserted into a threaded sleeve. US Patent Application No. 2004/0199169 to Koons shows a surgical apparatus which applies tension to a single strand of loop of wire held in loop by a cable end fitting, which is tensioned by the apparatus after which a ferrule is crimped on a cable to hold the selected tension of the loop. This is shown in use to retain a sternum after an open-heart procedure to secure the sternum together in FIG. 4 of Koons.

A strain relief tool secures a wire within an inner diameter of a sleeve to retain the wire without movement into a wall in U.S. Pat. No. 6,573,452 to Karlsson. A hermetic cable joint sleeve is shown in U.S. Pat. No. 6,272,273 to Bookwalter to splice a coaxial cable together and prevent exposure of the joint. The sleeve is crimped to retain each section of cable being spliced.

Several patents utilized in surgical procedures, a variety of tools and crimps are involved in securing a wire loop, similar to Koons, but using different crimping mechanisms, different tensioning tools and stated for use in different surgical procedures involving differing tissue attachments. These patent include U.S. Pat. No. 9,439,698 to Songer, U.S. Pat. No. 8,608,742 to Dell'Oca, U.S. Pat. No. 8,469,966 to Allen, U.S. Pat. No. 6,053,921 to Wagner and U.S. Pat. No. 5,569,253 to Farris. Wagoner utilizes a cable defining a leader portion which is a non-stranded wire less flexible than a main portion, the leader portion being made of steel, nylon or various plastics and the main portion preferably made from titanium or stainless steel. The cable is threaded through a common connector. In certain embodiments, the end of the main portion forms a tip having a diameter "substantially larger" than the diameter of the main portion. The tip is larger than a duct located within the connector with a stated purpose of preventing the cable from passing entirely through the ducts.

A crimp which is involved within a sleeve is shown in U.S. Pat. No. 8,795,343 to Stucki, which includes a common wire with a first end attaching a fixed buttress, FIG. 12, and a selectively applied clamping mechanism. The clamping mechanism involves a clamp and a clamping ring which rotatably attach to secure the clamp, containing a surgical cable within the clamp, which includes the inner diameter of the clamp collapsing around the cable, securing the wire within the clamp when fully applied within the sleeve by rotation. The clamp has a textured head which engages a lower surface of an application tool to provide rotation for insertion of the clamp within the clamp ring to reduce the inner diameter of the clamp.

In all of the above patents, the wire cable or pipe are all held static with the object being secured unable to move, bend or pivot. In the present apparatus is defined to include a surgical cable or wire having a first end providing a fixed or factory crimp, a corresponding first anchor sleeve providing a crimp end accepting the fixed or factory crimp in either an axial rotational or fixed connection, a second anchor sleeve and a surgically applied crimp collet, the second anchor sleeve defining a collet accepting end receiving the applied crimp collet in either an axial rotational or fixed connection, the crimp collet applied as a desired tension and cable length in order to collect the bone section within which each anchor sleeve in installed, gathering the bone section, while allowing some flexibility in the surgical cable between the installed anchor sleeves.

II. SUMMARY OF THE INVENTION

In the field of orthopedic surgery bones are generally approximated using screws, wires or pins to fix them in position. In some situations movement between bones is desired and should be retained. One important example is the re-approximation of the scaphoid to the lunate bones for repair of the scapho-lunate ligament. Other examples include motion between the first and second metacarpals with carpo-metacarpal arthroplasty or motion of the tibia and fibula at the ankle. Standard methods often reconnect these bones in a static fashion using screws or pins. A need exists for apparatus and methods that can approximate the bones and maintain this approximation while still allowing motion between them. The current techniques that use static screws or tendons or rotating screws that allow motion have not been overly successful.

Repairs are often required for injury induced instability between bones caused by various forms of disruptions including ligament disruption or tearing. For example, these instabilities include injury to the scapho-lunate ligament, disruption to the ligament between the radius and ulna at the wrist, wrist ligament injuries include lunate-triquetral ligament, scaphoid-trapezial ligament, and radio-carpal ligament, ankle sprain resulting in syndesmosis, age related instability such as between first and second metacarpals at the carpal metacarpal joint of the thumb, and other injuries of this general type.

Therefore, the apparatus and method of the present invention can be applied to repair any two adjacent bones where the physiological structures holding the bones approximated to each other have been damaged and the repair requires 1) that the bones be held in a position approximated to each other and 2) that the repair allows for motion between the two bones. It may also be used to attach portions of a common bone where the installation of the apparatus would benefit the alignment and healing of the common bone at the fracture site. The implants of the present invention can be manufactured as appropriate for the size of the bones to be repaired and the force that will be exerted on the implant after repair. In particular, when the implant is composed of a MFSS, the MFSS and be manufactured with various degrees of size, strength and flexibility as appropriate for the intended application.

Additionally, variations of use may involve the connection of soft tissue to a bone, the soft tissue comprising a ligament or tendon as attached to a bone. One or more strands of an implant wire, cable or suture attached to a soft tissue would be passed through a sleeve and traction applied to position the soft tissue to bone and an optimal position at which time a crimp would be secured to the implant to maintain bone and soft tissue positioning during healing. It is also contemplated that the present implant not only may be a cable, wire or suture, but a section of harvested graft from a tendon, ligament, allograft or other biologic. In this embodiment, the graft may be interposed between the structures being connected in order to promote healing. This can be accomplished by threading the suture or cable through a graft or placing the graft in some manner between the structures prior to engaging traction to position the graft or biologic between the torn or injured structures, the position of the graft or biologic is thereby maintained. It is further contemplated that the graft or biologic may be attached within a sleeve by a crimp and or suture or other means.

III. DESCRIPTION OF THE DRAWINGS

The following drawings are submitted with this utility patent application.

IV. DESCRIPTION OF THE PREFERRED EMBODIMENT

Figure 1:
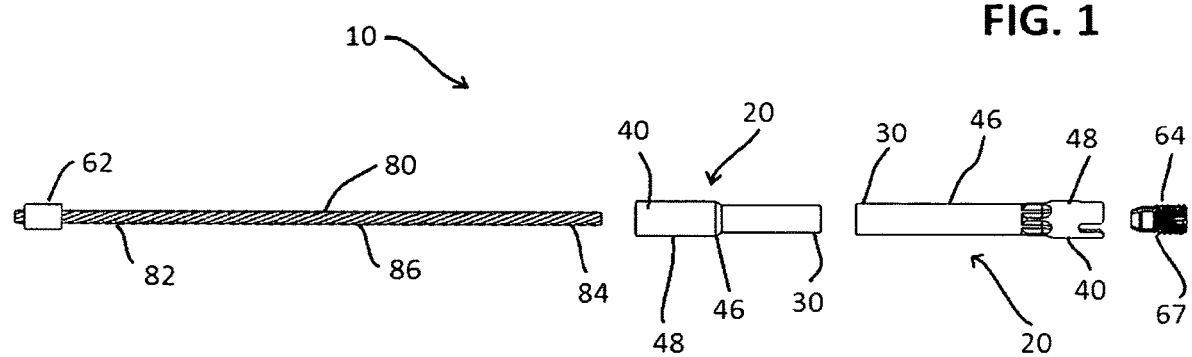
FIG. 1 is an extended side view of the components of the apparatus for the repair of bones and soft tissues.
Figure 2:
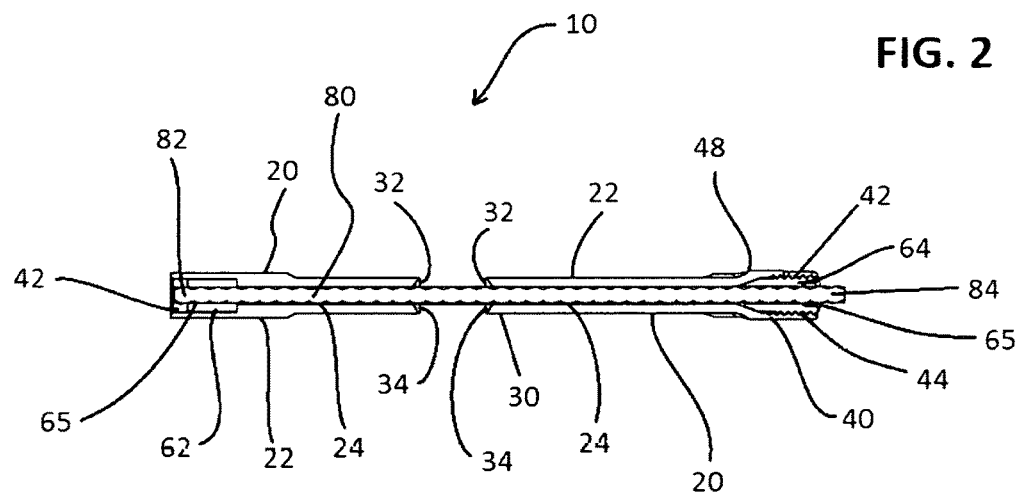
FIG. 2 is a side cross-sectional view of the apparatus in an assembled state.
Figure 3:
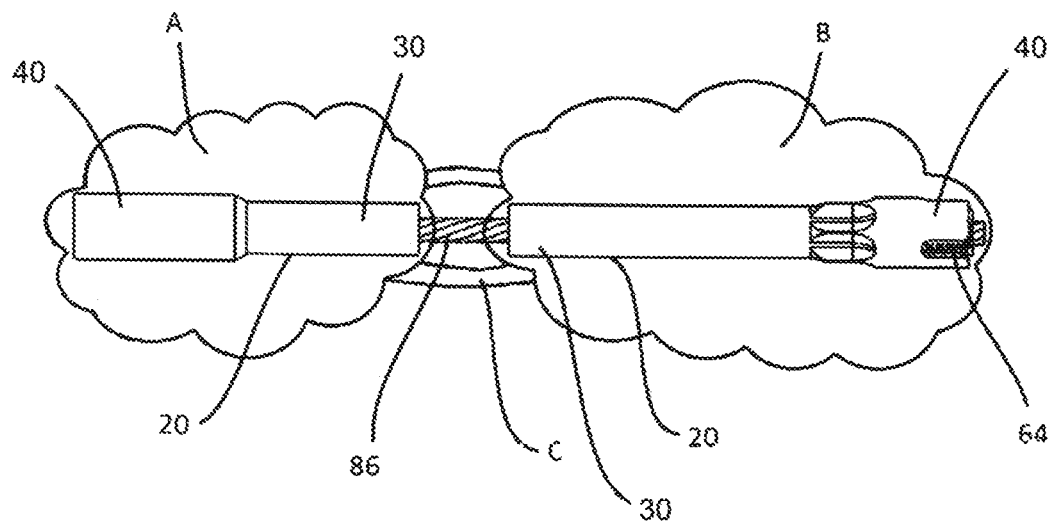
FIG. 3 is a representative side view of the apparatus as involved in the repair of two adjacent bones connected by soft tissue.
Figure 4:
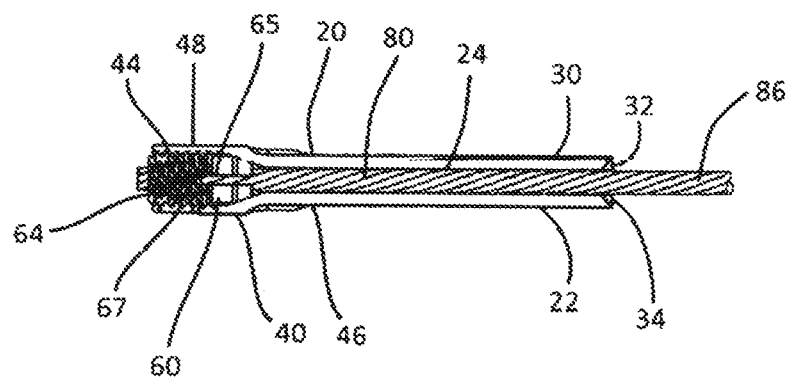
FIG. 4 is an isolated cross-sectional view of a sleeve having an adjustable crimp installed upon the implant.
Figure 5:
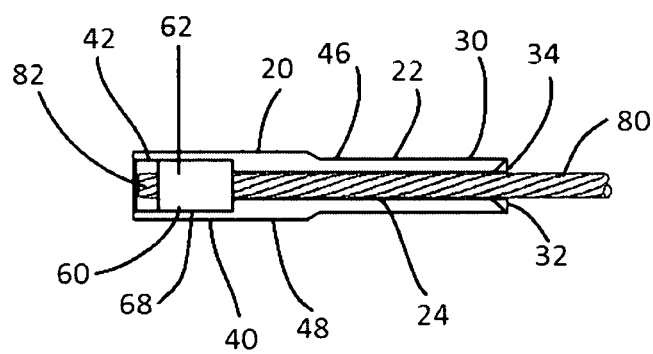
FIG. 5 is an isolated cross-sectional view of a sleeve having a fixed crimp installed upon the implant.
Figure 6:
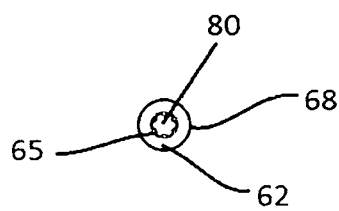
FIG. 6 is a sectional view of a first embodiment of a crimp having a circular formed outer perimeter engaging a cable implant.
Figure 7:
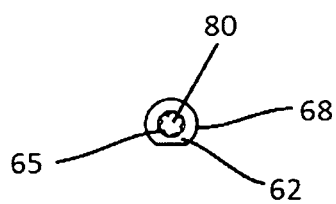
FIG. 7 is a sectional view of a second embodiment of a crimp having a circular formed outer perimeter including a flat portion on the outer surface engaging a cable implant.
Figure 8:
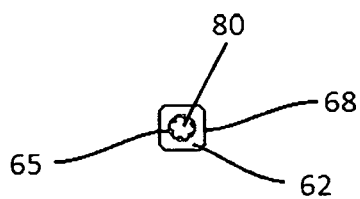
FIG. 8 is a sectional view of a third embodiment of a crimp having a square formed outer perimeter engaging a cable implant.
Figure 9:
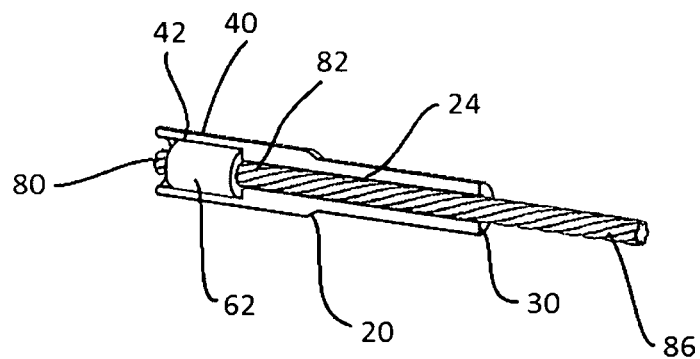
FIG. 9 is a perspective view of a sectional sleeve exposing the implant and a fixed crimp installed within the sleeve.

There currently is no adequate and reliable method to repair many of the ligaments and tendons between bones, particularly the scapho-lunate ligament. The particular challenge to be overcome is to apply an adequate traction force to bring multiple bones together and to hold them in a normally approximated position while still allowing a natural rotation and movement between the bones. The present apparatus, FIGS. 1-11 and 15, for the repair of bones, A, B, and soft tissues C includes the use of an implant composed of synthetic material that provides appropriate strength and allows motion which makes it advantageous for this type of repair. Both apparatus and methods using these implants with unique bone attachment and protection designed to address this problem are disclosed herein.

The methods, apparatus and drill guide of the present disclosure can be used to repair disruptions between many different bones and is not limited to any particular pair, triple, quartet, etc., of bones. In preferred embodiments, the apparatus is used to repair disruptions between bones of the hands, feet, wrists and ankles where it is important to maintain flexibility and rotational motion between the bones, FIGS. 3 and 10-11. In most preferred embodiments, the apparatus is applied to repair disruptions between the carpal bones of the hand including disruptions between the scaphoid and lunate, lunate-triquetral disruptions, scaphoid-trapezial disruptions, and radio-carpal disruptions and disruptions between bones of the ankle including the cuniforms, navicular, talus and cuboid. The present apparatus 10 comprises essentially an implant 80, at least two crimps 60 and two sleeves 20 which are installed within each bone A, B, involved in the repair, FIGS. 3 and 11.

Each sleeve 20, FIGS. 1-5 and 9, further comprises a body 22 defining an inner longitudinal bore 24 and an external surface 46, a first end 30 defining an opening 32, and a second end 40 defining a formed crimp aperture 42. It is preferable that the first end opening 32 defines a flared aperture 34, which presence will be further explained below relative to the implant 80. It is further preferable that the body 22 at the second end 40 defines a second end expansion 48. Installation of each sleeve 20 is prepared by first drilling a passage D into one involved bone after which the sleeve 20 is inserted into the drilled passage D with the first end 30 directed into the passage D. The drilled passage D may be conducted with two different drill bits, with a first boring being conducted by a narrower diameter drill bit and a second boring conducted with a wider diameter drill bit to contour the drilled passage D to the exterior surface 46 of a respective sleeve 20 with the second end expansion 48 fitted within the portion of the drilled passage D caused by the wider diameter drill bit in order that the second end expansion 48 gain secure purchase within the bore. Upon installation, each sleeve 20 should fit within the drilled passage D without lateral movement or play.

The implant 80, FIGS. 1-5 and 9-11, is at least one wire or cable defining a first end 82, an intermediate section 86 and a second end 84. The implant 80 is inserted through the respective inner longitudinal bores of each sleeve installed and secured in the bones to position and retain the adjacent bones A, B, in position relative to one another with some degree of flexibility between the bones and at an appropriate tension as desired by the surgeon. The intermediate section 86 is exposed between the first ends of each respective sleeve 20, the sleeves 20 having the respective first ends 30 directed towards one another. This intermediate section 86 thus has a capacity for flexion and a degree of angle similar to the tendon C which exists between the bones A, B, FIGS. 3 and 11. To enhance this angle and to remove any stress tension of sharp edge upon the section of implant emanating from each sleeve 20, the aforementioned flared aperture 34 in each first end 30 of each sleeve 20 allows for flexibility of angle and position of the implant in the intermediate section 86 to bend and flex out of each respective first end without containing a sharp or deforming edge, FIGS. 2 and 4-5.

The first end 82 and second end 84 of the implant have at least one crimp 60 applied to limit the implant length and distance and angle between the adjacent bone structures to that fixed by the surgeon. The crimps 60 are provided to engage a circumference of the implant 80 and adjust secure to the implant 80 at the desired location chosen by the surgeon. In this regard, the crimps define an inner implant passage 65 and an outer surface 66. Each crimp 60 may be provided in two alternatives—fixed 62 or adjustable 64. The fixed crimp 62 may be provided as factory installed on one end of the implant 80, while an adjustable crimp 64 may be applied by the surgeon once the implant 80 is installed through both sleeves 20 in the adjacent bones A, B, with the adjustable crimp 64 applied to limit the length and angle of the implant 80 at a proper location once the adjacent bones are gathered in an appropriate location and angle as selectively determined by the surgeon. The adjustable crimp 64 is manually secured to the implant 80 by the surgeon while the fixed crimp 62 is installed at the time of manufacture, or, quite possibly, prior to installation by the surgeon. For purpose of this description, a fixed crimp 62 may be incorporated into the implant itself, may be installed at the time of manufacture or affixed prior to installation. The adjustable crimp 64, for purpose of this description, would be considered a crimp 60 secured to the implant 80 prior to or during the surgical procedure. It is most preferable that once application of the crimps have been performed, any excess portion of the implant 80 extending beyond the applied crimps 60, either fixed or adjustable, be removed and have no extension beyond the margins of the crimps 60.

The sleeves 20 serve to secure the position of the implant 80 within the drilled passages D or bores and to protect the bone from degradation by the implant. The sleeves 20 reside over the implant 80 to secure the position of the implant 80. The sleeves 20 are used to align bores in bone and prevent the implant 80 from degrading the bone over time. The sleeves 20 can be provided with various features useful in the particular location in which they are used. The second end 40 of sleeve 20 may further provide a means for retaining the respective crimp 60, by way of a formed crimp aperture 42 or inner threads 44 contained within the inner longitudinal bore 24 of the second end 40, FIG. 15. In this regard, a corresponding crimp 60 may be provided with a formed outer perimeter 68 mating with the formed crimp aperture 42 to prohibit rotation of the crimp and attached implant 80, FIGS. 6-8. In another embodiment, the crimp 60 may provide an outer thread 67 in the outer surface 66 which engages the inner threads 44 contained within the inner longitudinal bore 24 of the second end 40. In yet another embodiment, the outer surface 66 of the crimp 60 may be tapered and provided with an outer thread 67 which, during rotational insertion within the inner threads 44 of the second end 40 of the respective sleeve 20, reduces the corresponding inner implant passage 65 of the crimp 60 as a means of securing the crimp 60 to the implant 80, FIG. 15.

For purposes of disclosure, the crimp 60 may be one of several means used to retain the implant within the sleeves 20 at a chosen length and tension. Other retaining means may include peg, crimp collar, wire collar, collar expansion, deformable sleeve, wire ring, shrink tubing other retaining means that can be secured to the implant 80. The second end 40 of the sleeve 20 may also be designed to accept a means of retaining an implant that does not have a retaining means thereon. For example, a sleeve 20 can be adapted to accept a screw, a screw-in multi-prong crimp, a peg, a deformable peg, or other retaining means. Therefore, as indicated, the crimp 60 or other retaining means is applied to securely to hold the implant 80 after forceful traction has been applied to approximate the bones and reduce the gap, as will be understood from the description herein.

A sleeve 20 would preferably be placed in the bone before the implant is placed. In another embodiment, the implant is placed first and the sleeves are passed over the implant and seated in the bone bores. In another embodiment, one sleeve 20, for a first bore in a first bone, can be placed on the implant 80 before implantation and another sleeve 20, for a second bore in a second bone, can be placed after implantation. Other combination methods can also be possible. The particular way in which the sleeves 20 and implants 80 are placed is determined for the disruption to be repaired taking into account the geometry of the bones, their size, the placement of the bores. These and other factors are to be taken into account as are particular to the repair of a disruption between any two particular bones A, B.

Sleeves 20 useful in the apparatus and methods of the present invention are advantageously composed of material that is biocompatible and sufficiently resistant to the wear that may be caused by contact with the implant under pressure and in motion. Sleeves 20 made of such materials can provide for a long lasting repair. In a preferred embodiment of the apparatus, sleeves 20 are composed of various biocompatible materials including stainless steel, various implantable metals, polyetheretherketone, ceramic, or any other material suitable for use with the material of the implant.

Figure 11:
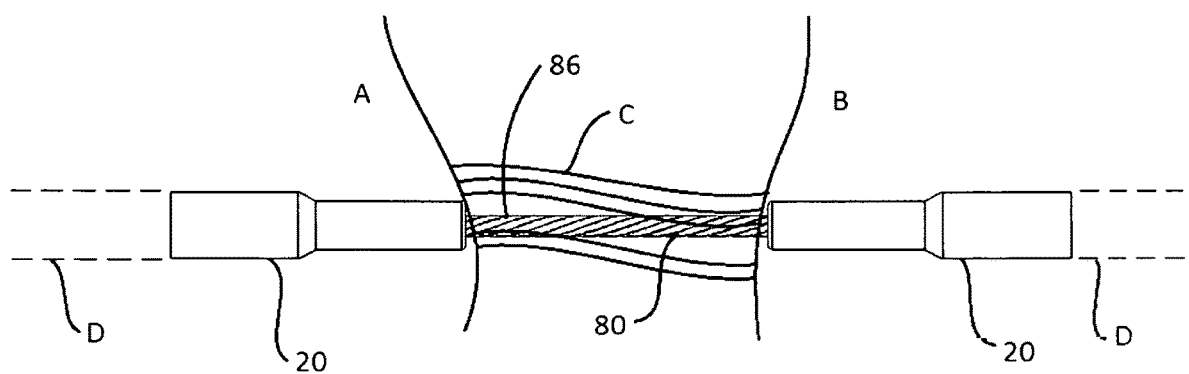
FIG. 11 is a side view of the apparatus installed within adjacent bones connected by an implant, with each sleeve installed within corresponding drill pathways within each bone, with the implant traversing a section of connecting soft tissue between the bones.

The size of the sleeves 20 is chosen as appropriate for the size of the bone, the diameter and the length of the bore in the bone. FIG. 11 shows two bones A, B, connecting by a tendon C, with sleeves 20 and an implant 80 in place. It is preferred that the sleeves 20 are slightly shorter than the length of the bore within each bone. The sleeve 20 should be placed adjacent the opening of the bore where the two bones are adjacent to each other, i.e., the middle of FIGS. 3 and 11, and slightly within the bone at the opening of the bore opposite, i.e., at the left and right sides of FIG. 11. This placement is preferred so that the sleeve 20 does not extend outside the bone, yet provides protection at the opening of the bore between the bones.

The apparatus is designed to provide a bone connection that will reduce the gap between the two bones bringing them securely together while at the same time allowing approximately 30 degrees of rotation of the scaphoid on the lunate. The use of strong flexible material in the implant 80 allows for this motion. The implant is secured in both bones. The apparatus also provides protection so that the implant 80 has a protective sleeve 20 allowing both simplified approximation of the bones and repetitive motion after repair without degradation of the bone. The implant 80 provides for time for collagen to form and tendons and ligaments C to heal. Final repair does not require removal of the implant 80 which continues to reside in the repair and provide additional strength and protection against re-injury.

It is preferable that the material of the implant 80 can be manufactured to exhibit varying degrees of flexibility. This allows one to use material with properties appropriate for the repair being performed. For example, when the implant 80 is used between bones where the natural articulation is high, a more flexible version of the material can be useful. When the implant 80 is used between bones with limited natural rotation relative to one another, a stiffer version of the material can be appropriate. When the material is used between bones where high forces are endured, a stronger version of the material can be used. Preferred materials meeting the above qualifications are flexible stainless steel wires or multifilament stainless steel cables. These materials can be designed and manufactured in a variety of diameters, strengths, deformability and torsional properties. These properties can be adjusted by using different designs, metallurgical mixtures and manufacturing techniques known in the art of metallurgy. It is also contemplated that the implant 80 may be provided with a leader of a reduced diameter, though not shown, which may be passed through the installed sleeves, the leader being incorporated within the implant or extending from the implant 80, and may be provided, where attached to the implant, with a breakaway detachment means to remove the leader upon installation and securing of the implant 80, the leader being available preferably on the end to which the surgically applied adjustable crimp 64 is located, also assisting in the threaded application of the crimp 60 to the implant 80.

The implant 80 may be supplied a single wire or cable, or may be supplied as more than one wire or cable providing two cable implants with an oval head adjustable crimp 64 which is fitted within a formed crimp aperture 42 in the sleeve 20, the crimp actually spreading the two cable implants apart and wedging each implant cable within the formed crimp aperture 42 with a bilateral force, with an enlarged oval portion of the crimp 60 rotated to produce the binding force to secure the implant cables within the second end 40 of the sleeve 20.

Figure 10:
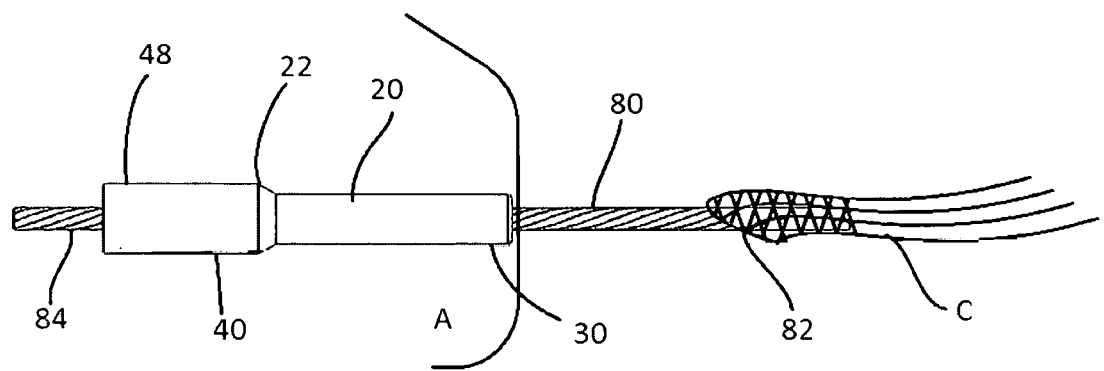
FIG. 10 is a side view of the implant and sleeve with the implant secured to a segment of soft tissue with the sleeve installed within a bone.

In furtherance of the apparatus, the implant 80 may comprise a graft harvested from a tendon or ligament C, an allograft or other biologic (hereinafter "graft"), FIGS. 10 and 11. This graft may be interposed between the structures being connected in order to promote healing, FIG. 10. This can be accomplished by threading the suture or cable through a graft or placing the graft in some manner between the structures prior to engaging traction to position the graft or biologic between the torn or injured structures to the with traction, the position of the graft or biologic is maintained. It is further contemplated that the graft or biologic may be attached within a sleeve by a crimp and or suture or other means. Some types of tendons which may be preferred include but are not limited to biceps tendons, rotator cuff tendons, patellar tendons, Achilles, or other joint involved tendons or ligaments.

A recommended drill guide 100 used in conjunction with the above apparatus is engineered to accurately enable the creation of bores in separate adjacent bones so that the bores meet at a target location between the bones. Guide pins which can be a K wire are placed accurately through the targeter drill guide. This can be an important part of a method for repairing a disruption due to the anatomy of joints. For example, the scapho lunate joint is only 3 to 4 mm wide and, due to the curvature of the bones this wire positioning has proved elusive. The use of the present drill guide 100 allows for accurate placement of guide pins.

One can also use the guide to pass the implant 80 (e.g.: MFSS cable) through each bone from either side. The target of the drill guide 100 at the joint is fashioned to facilitate the passage of the implant i.e., the target may be in the shape of a curved tube, a funnel, curved open u-channel or other shape that facilitates passage of the implant 80 between the bores.

Figure 12:
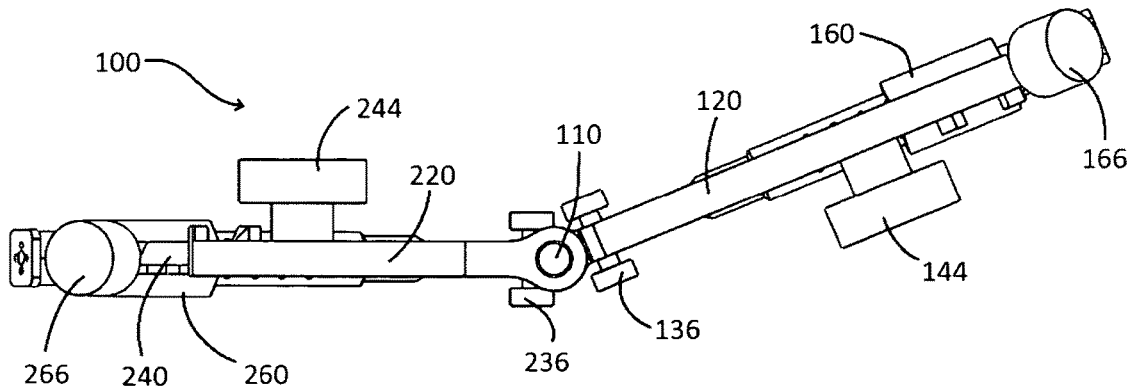
FIG. 12 is a top view of a drill guide.
Figure 13:
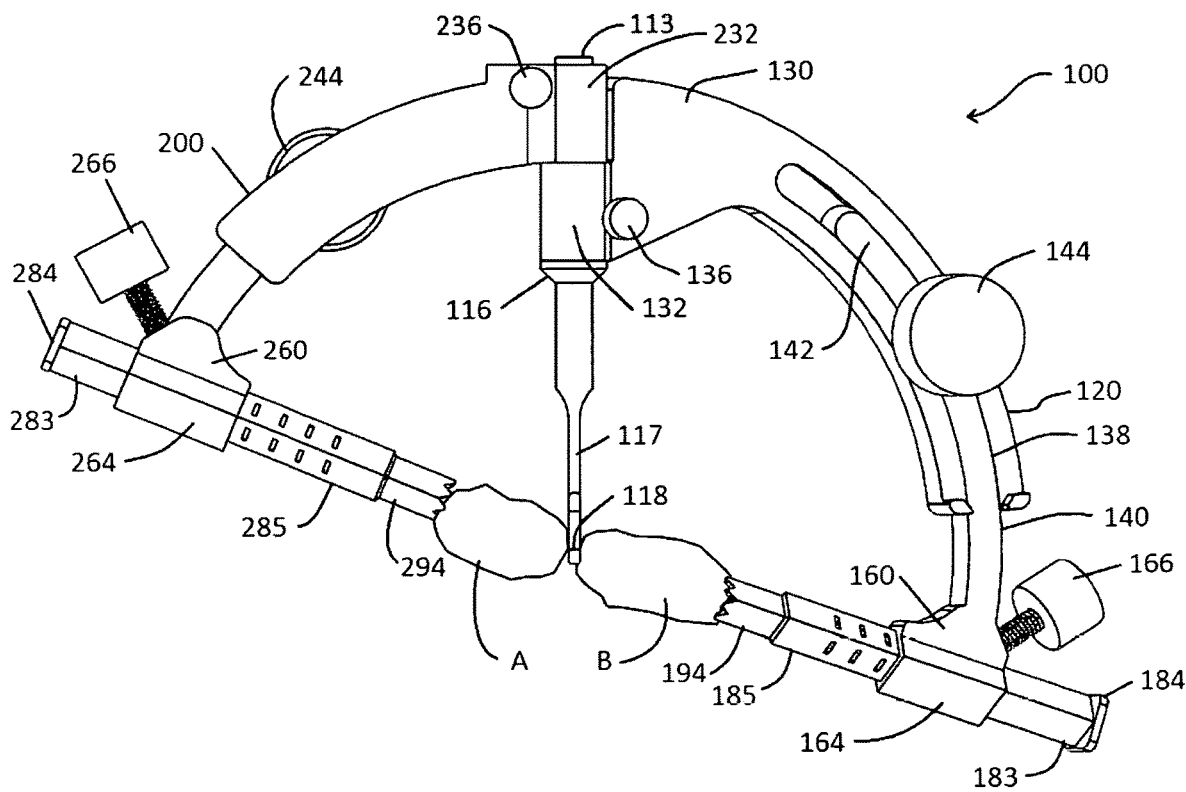
FIG. 13 is a side view of a drill guide.
Figure 14:
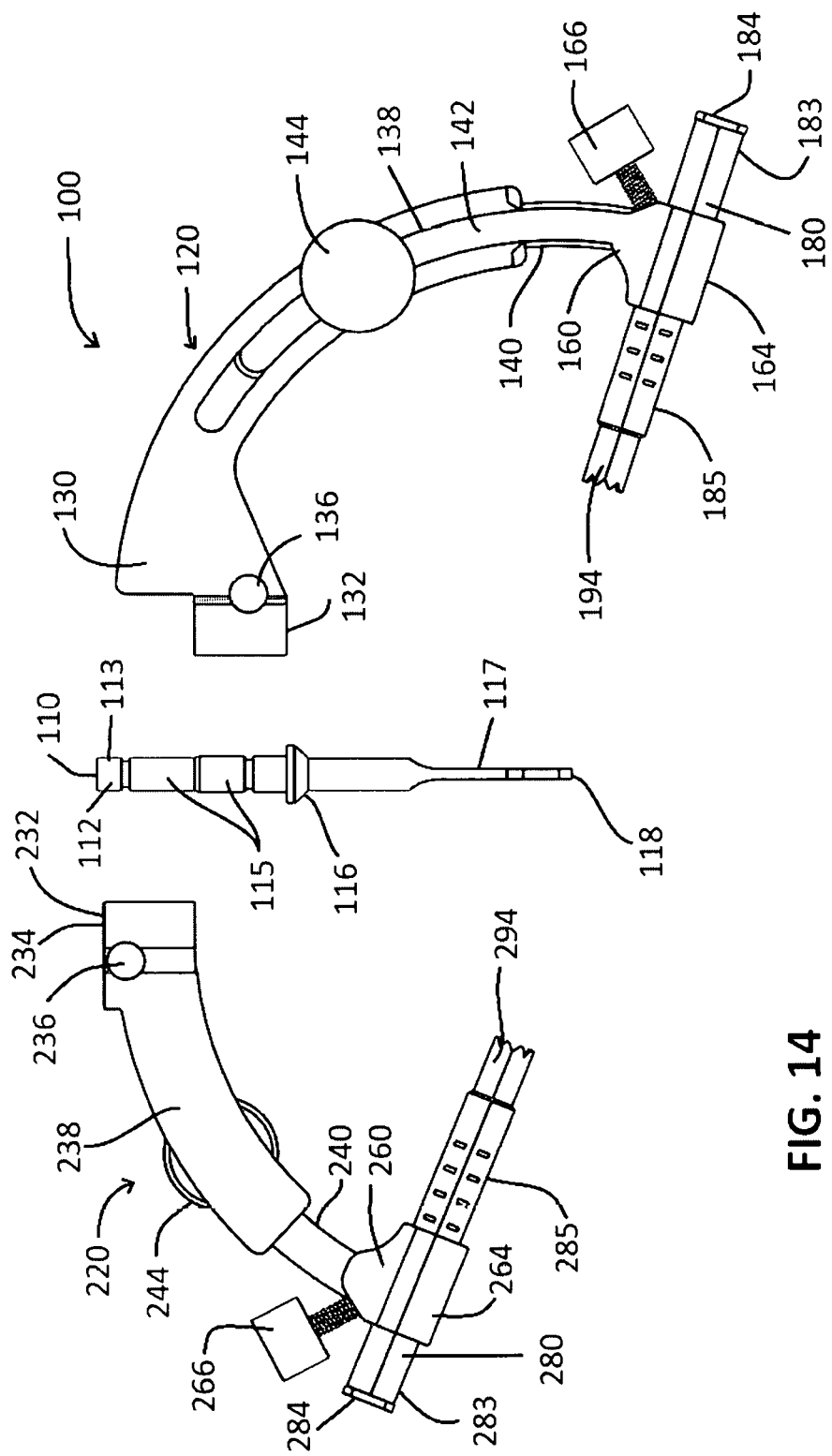
FIG. 14 is a side view of a drill guide having the first guide section and second guide section removed from a central pin.
Figure 15:
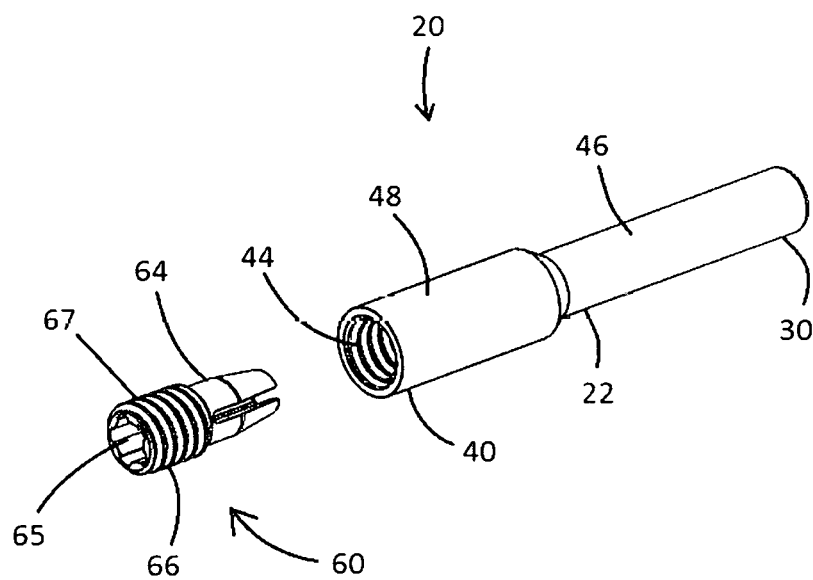
FIG. 15 is a perspective view of a second end of a sleeve with a formed crimp aperture having inner threads within a second end expansion, with an adjustable crimp defining outer threads within an outer surface and the inner implant passage within the adjustable crimp.

The drill guide 100, FIGS. 12-14, has a novel lateral swing mechanism with bilateral sides so that an accurate drill hole may be placed on the far, articular surface of the bone, within the joint, regardless of the size of the bone from two different directions coinciding with the proper angle desired by the surgeon applying the apparatus during surgical repair. The drill guide 100 comprises a central pin 110, a first guide section 120 and a second guide section 220 which target a location and provide a stable from two different directions towards a common intersection of the two drilled pathways converging at a common point. This corresponds to the location between the two bones A, B, where the implant 80 is passed between the two bones during repair using the above apparatus.

The central pin 110 defines an upper end 112 having an expanded head 113, a reduced swivel section 115, a lower expansion 116, and a lower end 117 terminating into a locator tip 118. The locator tip 118 provides a target indication where the drill pathways' D intersection will occur.

The first and second guide sections 120, 220, swivel around the reduced swivel section 115 in an axial rotation. Each first and second guide section 120 define a first section 130, 230, providing a respective swivel socket 132, 232, with a vertical bore 134, 234, a swivel locking means 136, 236, and a lower arcuate slide channel 138, 238. Each vertical bore 134, 234, of each swivel socket 132, 232, independently engages a portion of the common reduced swivel section 115, stacked on above the other, and may be locked into place upon the central pin 110 by engagement of each independent swivel locking means 136, 236.

Each first and second guide section 120, 220, further comprises a second section 140, 240, defining an arcuate slide arm 142, 242, which is slidably engaged within a respective lower arcuate channel 138, 238, of the first section 130, 230. The shape of the first and second sections defines an arc—hence the term arcuate to define them. The arcuate slide arm 142, 242, may be independently extended or retracted from the respective arcuate slide channel 138, 238, as determined by the location of the drill pathways, with the arcuate slide arm 142, 242, held at a position relative to the arcuate slide channel 138, 238, by a respective slide locking means 144, 244.

A third section 160, 260, further forms a drill tube socket 164, 264, within which a respective independent drill tube 180, 280, is inserted and retained. Each drill tube 180, 280, comprises an anchor section 182, 282, with a first end 183, 283, and a second end 185, 285, with a tapered target tip 194, 294. The first end 183, 283, may include a bushing 184, 284, to prevent direct rotational contact from a rotary drill to the first ends 183, 283, of each drill tube 180, 280. Within each respective drill tube socket 164, 264 each independent drill tube 180, 280, is slidably engaged. The relationship between the third section 160, 260, and the independent drill tubes 180, 280, provides a sliding extension allowing each tapered target tip 194, 294, to be placed in close proximity to each respective bone being drilled during the use of the drill guide 100 and the disclosed apparatus 10 implant pre-installation procedure. There is a locking means involved between the third sections 160, 260, and each independent drill tube 180, 280.

Other aspects of the drill guide 100 may include the expanded head 113 atop the central pin 110 being removable, allowing for the disassembly for cleaning of the instrument post surgery. Each guide section 120, 220, is allowed independent free rotation around the central pin 110 and freely with respect to each other. The swivel locking means 136, 236, slide locking means 144, 244, and slide locking means 166, 266, by example, can be a thumbscrew, as shown in the drawing figures, which is turned by the surgical staff to activate each locking means. Other swivel locking means can use pins, clamps, or other means commonly used in the art to fix a device from further movement.

The creation of a bore using the drill guide can be performed with a drill bit, a cannulated drill bit, a wire, a cannulated wire, using a lasers, by ablation with water jets, a reamer, an awl, an impaction drill, a shape memory coring device, or curved coring device, or other means known in the art. In preferred embodiments, the drill guide is used with a rotating drill bit or a wire. The drill bore has a native diameter of 2-4 mm, but may be constricted to smaller diameters by the installation of drill bushings. Drill bushings fit tightly to the native diameter, and have a smaller, concentric bore in them which can properly guide a smaller drill 0.062" or 1.5 mm for example. The long axes of the locator tip, optional drill bushings, and the drill bit are all coincident and intersect the target at the locator tip of the central pin. The overall size of the drill guide is made as appropriate for the sizes of the bones involved in the repair and the implant to be placed.

The locator tip 118 may provide a means of contact with the anatomy which allow for a stable connection to the anatomy, typically a bone. One means employs features that have roughness, coating or spikes at the point where the drill guide contacts the bone. The means provide a feature that can grip the bone surface more competently than if the lower end 117 of the central pin 110 had a smooth surface at the point of contact. The target at the base of the central pin 110 can also have such means on the faces of the target which will face bony anatomy.

The drill guide 100 also has means for stabilization and attachment to bony anatomy, not shown. As is common in the practice, a Kirschner wire (K-wire) is used like a stake to connect an instrument feature to a patient's bone. The central pin of the drill guide can have a hole, holes, a tube or tubes between 5-20 mm above the target. These holes or tubes can allow a K-wire to pass through the central post and then lodge into a patient's bone, thereby securing the drill guide in place with respect to that bone. Likewise, the end of the drill guide closest to the target can have a hole, holes and/or a tube or tubes through which a K-wire can be passed and lodge into a patient's bone, thereby securing the drill guide in place with respect to that bone.

In the use of this drill guide 100 for an SLL repair, the target would be lodged between the scaphoid and the lunate, which have been reduced per normal procedure. Placement of K-wires through the various stabilizing means stabilize the instrument as well as hold the bones in reduction. An x-ray could be used to verify position of the drill targeters and the target. A hole is drilled though each drill tube (with appropriate bushing installed) towards the target, stopping at the target. This allows for a measurement indicator which reports the bone size (same as hole length) to help the surgeon select the proper sleeve length and diameter. One may use the drill guide itself, as above, or may measure the bores directly. In the latter case, marked wires can be placed in the bores and observed on x-ray or fluoroscope.

Several methods may be employed involving the apparatus 10 in a variety of surgical repairs and procedures. In a first example, involves use of the apparatus 10 in repairing disruptions between a variety of bones as described above. In this example, an illustration of the application of the apparatus and methods of the apparatus use is presented as applied to the repair of a disruption between the scaphoid and lunate bones. Basic uses contemplated but not limited by the apparatus would include bone-to-bone for ligament repair, soft tissue to bone repair or other more specific uses as suggested by a surgeon having the apparatus available for use during orthopedic procedures. Briefly, in a bone-to-bone procedure, a first and second sleeve are implanted within adjacent bones and the implant is threaded through them, aligning the bones with proper tension and holding the tension by placement of the crimps intentionally applied by the surgeon to hold position during healing of the bones themselves or its connected soft tissue C, FIG. 11. In a similar fashion, wherein connection of a soft tissue C to a bone A, B, is desired, FIG. 10, the implant 80 is secured to the soft tissue C using various means including locking stitches, a cross lock or some other configuration so that one or more implants would emanate from the soft tissue C, further attaching within a sleeve 20 by use of a crimp 60 or other means to secure the implant 80 within the sleeve 20 and thereby maintain bone A, B and soft tissue C positioning to allow and promote healing.

Specific methods and uses would include a first use comprising the steps of creating an incision is made over the entry point to expose the first bone. In the case of a scapho lunate an incision is made on the radial aspect of the wrist over the scaphoid bone. A separate incision is made to expose the entry point into the second bone in this case the scapho-lunate joint and the lunate. The drill guide includes a means of securing the guide to the bone and to hold it in position. A Kirschner wire was placed through the securing means and into the scaphoid to secure the drill guide in a position aimed at the target at the far end of the scaphoid. The target is the central portion of the articular surface of the scaphoid bone at the joint with the lunate bone. The drill guide is positioned so that the drill bit follows the guide to reach the 'target' with, preferably, a variation of 1 mm or less. The bore was then drilled in the scaphoid bone. A second Kirshner Wire is placed for use as a 'joy stick' to rotate and reduce the lunate bone into a position approximating a normal alignment with the scaphoid bone. A second drill guide is placed on the lunate bone and directed to the target. This guide can also be secured to the lunate bone with a Kirshner wire. The target of the lunate is the central portion of the articular surface of the lunate bone at the joint with the scaphoid bone. Thus the target area of the lunate and the target area of the scaphoid align with each other at the articular surfaces of the two bones. The lunate bone was then drilled using the drill guide and so that the bore exits the lunate bone at the target area.

An implant 80 was prepared for the repair. In this case, an implant 80 composed of a multifilament stainless steel cable (MFSS) was employed to repair the disruption. The implant 80 is provided with a crimp 60 at one end that will seat in a sleeve 20 adapted to accept it. In this case, it is the sleeve 20 placed in the lunate bone. A measurement of the length of the implant 80 required for the repair is obtained by taking the distance from the entry point on the lunate, through the lunate target area, through the scaphiod target area and to the entry point of the bore in the scaphoid bone. The measurement was obtained by measuring laser marks that had been placed on the Kirshner wires placed through the bores in the scaphoid and lunate bones. Sleeves 20 of appropriate size were then chosen for insertion into the bores. The sleeves 20 were of a diameter that fit into the bores and cannulated to accept the implant 80. The end of one of the sleeves 20, in this case the end that is to be located at the entry point of the lunate bone, was adapted to accept a crimp 60 that is present on the implant 80. An end of the other sleeve 20, in this case the end of the sleeve 20 that is to be seated at the entry of the bore in the scaphoid bone, was adapted to accept the adjustable crimp 64 having the outer thread 67.

One end of the implant 80 is fitted with a fixed crimp 62 that will seat into the end of the sleeve 20 for the lunate bone as described above. The sleeve 20 that will reside in the lunate is then passed over the implant 80 so that the end adapted for the crimp 60 is properly aligned with the crimp 60 on the implant 80. The implant 80 is then passed through the bores in both bones, from lunate to scaphoid, leaving the sleeve 20 for the lunate and the crimp 60 external to the lunate bone. The sleeve 20 for the scaphoid bone is then passed over the implant 80. The sleeves 20 were then inserted into the bores in the bones. Traction was applied to the implant 80 at the far end of the scaphoid so that crimp 60 seats in the sleeve 20 in the lunate and the position of the bones and the scapho-lunate gap is corrected. The implant 80 is then secured in the sleeve 20 in the scaphoid bone by applying the adjustable crimp 64 providing the outer thread 67.

Testing of the implant 80 was conducted by applying traction to the implant 80 at the radial side of the scaphoid and observing the scapho-lunate joint reduce and narrow bringing the two bones together. The scaphoid was held in a horizontal position while maintaining the ability to rotate 10 to 20 into a vertical position. This testing demonstrated the applicability of the implant 80 to easily placed and to provide motion, including rotational motion, in a joint between two bones—in this case the scaphoid and lunate bone.

Other methods and applicable uses of the apparatus would be evident by those skilled in the surgical arts. For example, the apparatus 10 and drill guide 100 can be used in a singular bone repair, repair of aligned bones including vertebra, ribs, sternum, long bones, bones involved in joints, bone fusion, bone grafting, skull repair, angular bone formation, tendon and ligament repair, and other surgical procedures which would involve a bone tendon or ligament, or attachment thereto. It would be contemplated that slight and moderate modification to the essential claimed component subject matter may be provided to adapt the apparatus and drill guide to a suitable alternative surgical procedure. While the apparatus 10, drill guide 100 and methods disclosed herein have been particularly shown and described with reference to a preferred embodiment thereof, it will be understood by those skilled in the art that changes in form and detail may be made therein without departing from the spirit and scope of the invention.

What is claimed is:

1. An apparatus for repair of disruption between the scaphoid and lunate bones and maintaining flexibility and rotational motion between the scaphoid and lunate bones and soft tissues, the apparatus comprising:

a scaphoid sleeve and a lunate sleeve, each of said sleeves defining a cylindrical body, an inner longitudinal bore, an external bone-engaging surface, a first end defining an opening with a flared aperture, and a second end defining a crimp aperture and a second end expansion, larger than the body, each of said sleeves configured to be independently installed in a drilled passage within each of the scaphoid and lunate bones, respectively;

at least one implant comprising a wire or cable or strand of a graft harvested from a tendon or ligament, said at least one implant having a first end, an intermediate section and a second end, said at least one implant inserted through said inner longitudinal bores of said sleeves, said at least one implant providing flexibility between the scaphoid and lunate bones and soft tissue at a tension as determined by an installing surgeon; and said sleeves being configured to traverse substantially through the entire length of said drilled passages through which the implant will pass; and a fixed crimp and an adjustable crimp applied to limit an implant length, distance and angle between said scaphoid and lunate bones and said soft tissues to a position as determined by the surgeon, the adjustable crimp defining an outer surface and an inner implant passage securely engaging a circumference of said at least one implant, wherein the external bone-engaging surface of each sleeve is devoid of threads, wherein the crimp aperature of one of the sleeves is a formed crimp aperture provided with inner threads contained within said inner longitudinal bore and the crimp aperature of the other sleeve is a fixed crimp aperture, wherein the crimp aperture of the scaphoid sleeve is provided with inner threads contained within said inner longitudinal bore, wherein the fixed crimp is secured to the first end of the implant prior to a surgical procedure, and resides within the fixed crimp aperture of a sleeve, wherein the adjustable crimp is secured to the second end of the implant during the surgical procedure, and resides within the formed crimp aperture of a sleeve, wherein the adjustable crimp comprises a tapered distal end and a cylindrical proximal end, wherein the outer surface of said cylindrical proximal end comprises outer threads, wherein during rotational insertion of said adjustable crimp within said formed crimp aperture the outer threads of the adjustable crimp engages the inner threads contained within the inner longitudinal bore of the formed crimp aperture and reduces the inner implant passage of the adjustable crimp to firmly secure the adjustable crimp to the second end of the implant, wherein each second end expansion is configured to prevent lateral movement or play of said sleeves within said drilled passages, wherein, when the apparatus is implanted, said first ends of each respective sleeve are directed towards one another at an angle allowing up to 30 degrees of flexion within said at least one implant, wherein, when the apparatus is implanted, the intermediate section of the at least one implant is exposed between the first ends of the sleeves and has a capacity for flexion and a degree of angle similar to a tendon between the scaphoid and lunate bones.

2. The apparatus as disclosed in claim 1, said sleeves comprise:
   a biocompatible material including stainless steel, polyetheretherketone (PEEK) or ceramic.

3. The apparatus of claim 1 wherein substantially an entirety of the external bone contacting surface of at least one of said sleeves is entirely smooth.

4. The apparatus of claim 1 wherein the fixed crimp is a factory installed crimp on said first end of said at least one implant.

\* \* \* \* \*